(12) United States Patent
Ino et al.

(10) Patent No.: US 9,226,884 B2
(45) Date of Patent: *Jan. 5, 2016

(54) LIQUID CLEANSING COMPOSITION

(71) Applicant: AJINOMOTO CO., INC., Chuo-ku (JP)

(72) Inventors: Masahiro Ino, Kawasaki (JP); Naoaki Ikeda, Kawasaki (JP); Takanori Sugimoto, Kawasaki (JP)

(73) Assignee: AJINOMOTO CO., INC., Chuo-ku (JP)

( * ) Notice: Subject to any disclaimer, the term of this patent is extended or adjusted under 35 U.S.C. 154(b) by 116 days.

This patent is subject to a terminal disclaimer.

(21) Appl. No.: 14/064,454

(22) Filed: Oct. 28, 2013

(65) Prior Publication Data

US 2014/0051651 A1  Feb. 20, 2014

Related U.S. Application Data

(63) Continuation of application No. PCT/JP2012/061431, filed on Apr. 27, 2012.

(30) Foreign Application Priority Data

Apr. 28, 2011 (JP) .................. 2011-102517

(51) Int. Cl.
*A61K 8/44* (2006.01)
*A61K 8/60* (2006.01)
*A61K 8/42* (2006.01)
*C11D 1/29* (2006.01)
*C11D 1/66* (2006.01)
*C11D 3/33* (2006.01)
*A61K 8/46* (2006.01)
*A61Q 5/02* (2006.01)
*A61Q 19/10* (2006.01)
*A61Q 19/00* (2006.01)

(52) U.S. Cl.
CPC . *A61K 8/42* (2013.01); *A61K 8/442* (2013.01); *A61K 8/463* (2013.01); *A61K 8/604* (2013.01); *A61Q 5/02* (2013.01); *A61Q 19/007* (2013.01); *A61Q 19/10* (2013.01); *C11D 1/29* (2013.01); *C11D 1/66* (2013.01); *C11D 3/33* (2013.01)

(58) Field of Classification Search
CPC ......... A61K 8/60; A61K 8/602; A61K 8/604; A61K 8/44; A61K 8/442
See application file for complete search history.

(56) References Cited

U.S. PATENT DOCUMENTS

| | | | |
|---|---|---|---|
| 4,673,525 A * | 6/1987 | Small et al. .................. | 510/151 |
| 5,147,868 A | 9/1992 | Graham et al. | |
| 5,529,712 A | 6/1996 | Sano et al. | |
| 5,646,100 A * | 7/1997 | Haugk et al. .................. | 510/131 |

FOREIGN PATENT DOCUMENTS

| | | |
|---|---|---|
| CN | 1874750 A | 12/2006 |
| CN | 101801333 A | 8/2010 |
| EP | 0 010 573 A1 | 5/1980 |
| EP | 0 648 833 A1 | 4/1995 |
| JP | 55-40669 | 3/1980 |
| JP | 2005-325188 | 11/2005 |
| WO | WO 94/22994 A1 | 10/1994 |

OTHER PUBLICATIONS

U.S. Appl. No. 14/064,659, filed Oct. 28, 2013, Ino, et al.
Preliminary Search Report issued Nov. 8, 2013 in French Patent Application No. 1253899 (with English translation of category of Cited Documents).
Written Opinion issued Apr. 27, 2012 in French Patent Application No. FR 1253899 (with English translation).
International Search Report issued Jul. 31, 2013 in PCT/JP2012/061431 (with English translation).

* cited by examiner

*Primary Examiner* — Jonathan S Lau
(74) *Attorney, Agent, or Firm* — Oblon, McClelland, Maier & Neustadt, L.L.P.

(57) ABSTRACT

Combining a particular alkenoic acid or salt thereof with a sugar type surfactant and/or sulfate type surfactant affords a liquid cleansing composition which provides a good amount of lather and a superior moist feeling after washing.

21 Claims, No Drawings

LIQUID CLEANSING COMPOSITION

TECHNICAL FIELD OF THE INVENTION

The present invention relates to a particular alkenoic acid or a salt thereof, and a liquid cleansing composition containing a sugar type surfactant and/or a sulfate type surfactant.

BACKGROUND OF THE INVENTION

In recent years, a liquid cleansing composition containing a sugar type surfactant and/or a sulfate type surfactant as a surfactant has been used. While the liquid cleansing composition is superior in the amount of lather, it often causes a dry feeling after washing. To improve such dry feeling and to provide moist feeling after washing, a moisturizer has been conventionally added. However, addition of a moisturizer gives rise to a concern about a decrease in the amount of lather.

In addition, a liquid cleansing composition preferably has not only good lather amount but also appropriate viscosity affording good sense of use. Concretely, this is because an appropriate viscosity of a liquid cleansing composition resists easy sagging from palm during use, thus improving handling property, a rich texture adds a premium feeling to the liquid cleansing composition, and the like. To achieve an appropriate viscosity of a liquid cleansing composition, a natural polymer and/or a synthetic polymer and the like have been conventionally used. However, in this case also, addition of a moisturizer in an attempt to provide a moist feeling after washing gives rise to a concern about a decrease of viscosity.

SUMMARY OF THE INVENTION

Problems to be Solved by the Invention

It is an object of the present invention to provide a liquid cleansing composition having a good amount of lather and superior in the moist feeling after washing.

Means of Solving the Problems

The present inventors have conducted intensive studies in an attempt to solve the aforementioned problems and found that the above-mentioned problem can be solved by combining a particular alkenoic acid or a salt thereof with a sugar type surfactant and/or a sulfate type surfactant, which resulted in the completion of the present invention.

Accordingly, the present invention provides the following.
[1] A liquid cleansing composition comprising
(Component A) a compound represented by the formula (1)

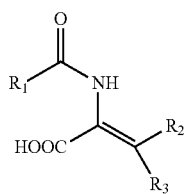

(1)

wherein $R_1$ is a saturated or unsaturated, linear or branched-chain hydrocarbon group having a carbon number of 7 to 25, and $R_2$ and $R_3$ are each independently a hydrogen atom or an alkyl group having a carbon number of 1 to 6, preferably a carbon number of 1 to 5, or a salt thereof, and
(Component B) a sugar type surfactant and/or a sulfate type surfactant.
[2] The liquid cleansing composition of [1], wherein $R_1$ is a saturated or unsaturated, linear or branched-chain hydrocarbon group having a carbon number of 9 to 13.
[3] The liquid cleansing composition of [1] or [2], wherein one of $R_2$ and $R_3$ is a methyl group, and the other is a hydrogen atom.
[4] The liquid cleansing composition of [1], wherein component A is 2-dodecanamido-2-butenoic acid or a salt thereof.
[5] The liquid cleansing composition of any of [1] to [4], wherein the content of component A is not less than 0.0001 wt % and not more than 1 wt % of the liquid cleansing composition.
[6] The liquid cleansing composition of any of [1] to [5], wherein the sugar type surfactant is alkylglucoside.
[7] The liquid cleansing composition of any of [1] to [6], wherein the sulfate type surfactant is polyoxyethylene alkyl ether sulfuric acid or a salt thereof.
[8] The liquid cleansing composition of any of [1] to [7], further comprising (Component C) a polysaccharide-type polymer.
[9] The liquid cleansing composition of [8], wherein component C is one or more kinds selected from the group consisting of xanthan gum, carageenan, locust bean gum, guar gum, pectin and succinoglycan.
[10] A cosmetic agent comprising the liquid cleansing composition of any of [1] to [9].
[11] A method of preparing a liquid cleansing composition comprising (Component B) a sugar type surfactant and/or a sulfate type surfactant, and superior in a moist feeling after washing, which comprises a step of adding
(Component A) a compound represented by the formula (1)

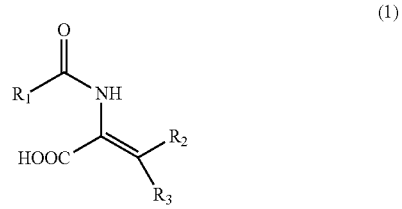

(1)

wherein $R_1$ is a saturated or unsaturated, linear or branched-chain hydrocarbon group having a carbon number of 7 to 25, and $R_2$ and $R_3$ are each independently a hydrogen atom or an alkyl group having a carbon number of 1 to 6, preferably a carbon number of 1 to 5, or a salt thereof.
[12] The method according to [11], wherein $R_1$ is a saturated or unsaturated, linear or branched-chain hydrocarbon group having a carbon number of 9 to 13.
[13] The method according to any one of [11] or [12], wherein one of $R_2$ and $R_3$ is a methyl group and the other is a hydrogen atom.
[14] The method according to [11], wherein Component A is 2-dodecanamido-2-butenoic acid or a salt thereof.
[15] The method according to any one of [11] to [14], wherein Component A is added such that the content of Component A in the liquid cleansing composition is not less than 0.0001 wt % and not more than 1 wt % of the liquid cleansing composition.
[16] The method according to any one of [11] to [15], wherein the sugar type surfactant is alkylglucoside.

[17] The method according to any one of [11] to [16], wherein the sulfate type surfactant is polyoxyethylene alkyl ether sulfuric acid or a salt thereof.

[18] The method according to any one of [11] to [17], further comprising a step of adding (Component C) a polysaccharide-type polymer.

[19] The method according to [18], wherein Component C is one or more kinds selected from the group consisting of xanthan gum, carageenan, locust bean gum, guar gum, pectin and succinoglycan.

Effect of the Invention

A liquid cleansing composition having a good amount of lather and superior in a moist feeling after washing can be provided by adding a particular alkenoic acid or a salt thereof to a liquid cleansing composition containing a sugar type surfactant and/or a sulfate type surfactant.

DESCRIPTION OF EMBODIMENTS (Component A)

The alkenoic acid of component A to be used in the present invention is a compound represented by the formula (1)

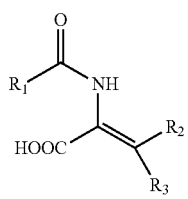

(1)

wherein $R_1$ is a saturated or unsaturated, linear or branched-chain hydrocarbon group having a carbon number of 7 to 25, and $R_2$ and $R_3$ are each independently a hydrogen atom or an alkyl group having a carbon number of 1 to 6, preferably a carbon number of 1 to 5.

$R_1$ is a saturated or unsaturated, linear or branched-chain hydrocarbon group having a carbon number of 7 to 25. The carbon number is preferably 7 to 21, more preferably 7 to 15, further preferably 9 to 15, most preferably 9 to 13. The hydrocarbon group is preferably an alkyl group, specifically, a group having a carbon number of 7 to 25, such as a heptyl group, an octyl group, a nonyl group, a decyl group, an undecyl group, a tridecyl group, a tetradecyl group, a pentadecyl group, a heptadecyl group, an octadecyl group, a nonadecyl group, an icosyl group, an eicosyl group, a henicosyl group, a heneicosyl group, a docosyl group, a tricosyl group, a tetracosyl group, a pentacosyl group, an isoheptyl group, an isooctyl group, an isononyl group, an isodecyl group, an isoundecyl group, an isotridecyl group, an isotetradecyl group, an isopentadecyl group, an isoheptadecyl group, an isooctadecyl group, an isononadecyl group, an isoicosyl group, an isoeicosyl group, an isohenicosyl group, an isoheneicosyl group, an isodocosyl group, an isotricosyl group, an isotetracosyl group, an isopentacosyl group and the like. From the aspect of solubility of component A, a group having a carbon number of 7 to 15, such as a heptyl group, a nonyl group, an undecyl group, a tridecyl group, a pentadecyl group and the like, is preferable, a group having a carbon number of 9 to 13, such as a nonyl group, an undecyl group, a tridecyl group and the like, are more preferable, and an undecyl group is most preferable.

$R_2$ and $R_3$ are each independently a hydrogen atom or an alkyl group having a carbon number of 1 to 6. The alkyl group having a carbon number of 1 to 6 may be linear or branched-chain. Examples thereof include a methyl group, an ethyl group, a propyl group, an isopropyl group, a butyl group, an isobutyl group, a sec-butyl group, a tert-butyl group, a pentyl group, an isopentyl group, a neopentyl group, a 1,2-dimethylpropyl group, a 1-ethylpropyl group, a hexyl group, a isohexyl group, a 1,1-dimethylbutyl group, a 2,2-dimethylbutyl group, a 3,3-dimethylbutyl group, a 1-ethylbutyl group, and the like. Among these, an alkyl group having a carbon number of 1 to 5 is preferable, an alkyl group having a carbon number of 1 to 4 is more preferable, an alkyl group having a carbon number of 1 to 3 is further preferable, a methyl group, an ethyl group and a propyl group are particularly preferable, and a methyl group is most preferable. One of $R_2$ and $R_3$ is preferably an alkyl group having a carbon number of 1 to 6, and the other is preferably a hydrogen atom, and one of $R_2$ and $R_3$ is more preferably a methyl group, and the other is more preferably a hydrogen atom.

Examples of the alkenoic acid for component A include 2-decanamido-2-butenoic acid, 2-decanamido-2-pentenoic acid, 2-decanamido-2-hexenoic acid, 2-decanamido-2-heptenoic acid, 2-decanamido-2-octenoic acid, 2-dodecanamido-2-butenoic acid, 2-dodecanamido-2-pentenoic acid, 2-dodecanamido-2-hexenoic acid, 2-dodecanamido-2-heptenoic acid, 2-dodecanamido-2-octenoic acid, 2-tetradecanamido-2-butenoic acid, 2-tetradecanamido-2-pentenoic acid, 2-tetradecanamido-2-hexenoic acid, 2-tetradecanamido-2-heptenoic acid, 2-tetradecanamido-2-octenoic acid and the like. Among these, 2-dodecanamido-2-butenoic acid, 2-tetradecanamido-2-butenoic acid and 2-decanamido-2-hexenoic acid are preferable, and 2-dodecanamido-2-butenoic acid is particularly preferable.

The alkenoic acid for component A of the present invention may be in the form of a salt. While the salt is not particularly limited, for example, alkali metal salt such as sodium salt, potassium salt, lithium salt and the like; alkaline earth metal salt such as calcium salt, magnesium salt and the like; ammonium salt such as alkanol amine salt and the like; basic organic compound salt and the like can be mentioned. From the aspect of solubility, sodium salt, potassium salt and ammonium salt are preferable, sodium salt and potassium salt are more preferable, and sodium salt is most preferable.

Component A has an alkanamide group in the structure thereof, as shown in the formula (1), it has appropriate hydrophobicity, and therefore, easily absorbs to the skin, and can afford a moisturizing effect even when used in combination with a surfactant that causes a strong dry feeling, such as a sugar type surfactant and a sulfate type surfactant.

Component A can be produced by a known method. For example, component A can be prepared by heating alkylamide and 2-ketoalkanoic acid under reflux in a solvent, and condensing the mixture. Examples of alkylamide include laurylamide, myristylamide, palmitylamide, stearylamide, coconut oil alkylamide and the like. Examples of 2-ketoalkanoic acid include 2-ketobutanoic acid, 2-ketopentanoic acid, 2-ketohexanoic acid and the like. As the solvent, any aprotonic solvent can be used without any particular limitation. For example, toluene, xylene, N,N-dimethylformamide, dimethyl sulfoxide and the like can be mentioned.

The content of component A in the liquid cleansing composition of the present invention is not particularly limited as long as it can impart moisturizing property. It is preferably 0.0001 wt % or more, more preferably 0.001 wt % or more, further preferably 0.002 wt % or more, further more preferably 0.004 wt % or more, still more preferably 0.006 wt % or more, further still more preferably 0.01 wt % or more, especially preferably 0.02 wt % or more, further especially preferably 0.04 wt % or more, of the liquid cleansing composition. In addition, the content of component A is preferably 1 wt % or less, more preferably 0.5 wt % or less, further preferably 0.4 wt % or less, still more preferably 0.3 wt % or less, especially preferably 0.1 wt % or less. In the present specification, "weight" and "mass" are to be considered synonymous, and "wt %" and "parts by weight" are to be considered synonymous with "mass %" and "parts by mass".

(Component B)

The liquid cleansing composition of the present invention contains (Component B) a sugar type surfactant and/or a sulfate type surfactant as a main component.

Examples of the sugar type surfactant include sorbitol fatty acid ester such as sorbitol monolaurate, sorbitol monostearate, sorbitol monooleate, sorbitol trioleate, sorbitol tristearate, sorbitol monoisostearate and the like; sorbitan ester of fatty acid such as sorbitan isostearate, sorbitan olivate, sorbitan oleate, sorbitan caprylate, sorbitan dioleate, sorbitan distearate, sorbitan stearate, sorbitan sesquiisostearate, sorbitan sesquioleate, sorbitan sesquicaprylate, sorbitan sesquistearate, sorbitan triisostearate, sorbitan trioleate, sorbitan tristearate, sorbitan palmitate, sorbitan cocoate, sorbitan laurate; sucrose ester of fatty acid such as sucrose acetate isobutyrate, sucrose octaacetate, sucrose oleate, sucrose distearate, sucrose dilaurate, sucrose stearate, sucrose tetraisostearate, sucrose tetrahydroxystearate, sucrose tristearate, sucrose tribehenate, sucrose tetrastearate triacetate, sucrose palmitate, sucrose hexaerucate, sucrose hexapalmitate, sucrose pentaerucate, sucrose pentahydroxystearate, sucrose polyoleate, sucrose polystearate, sucrose polysoyate, sucrose polypalmate, sucrose polybehenate, sucrose polylaurate, sucrose polylinoleate, sucrose polycottonseedate, sucrose myristate, sucrose cocoate, sucrose laurate, sucrose ricinoleate, sucrose benzoate, acetylated sucrose distearate, sucrose tetrastearate triacetate; alkyl glucoside such as coconut oil fatty acid glucoside, lauryl glucoside, decyl glucoside, myristyl glucoside, palmityl glucoside, stearyl glucoside, coco glucoside and the like; and the like. These may be used alone or two or more kinds thereof may be used in combination.

Of the above-mentioned sugar type surfactants, alkyl glucoside is preferable. Among these, coconut oil fatty acid glucoside, lauryl glucoside and decyl glucoside are more preferable. From the aspect of viscosity, lauryl glucoside is more preferable. In addition, a combined use of coconut oil fatty acid glucoside or decyl glucoside, and lauryl glucoside is also preferable.

Examples of the sulfate type surfactant include alkyl sulfuric acid such as sodium lauryl sulfate, potassium lauryl sulfate, sodium myristyl sulfate, potassium myristyl sulfate, sodium palmityl sulfate, sodium stearyl sulfate, sodium oleyl sulfate, triethanolamine lauryl sulfate and the like and salts thereof; polyoxyethylene alkyl ether sulfuric acid such as polyoxyethylene lauryl ether sodium sulfate, polyoxyethylene cetyl ether sodium sulfate, polyoxyethylene oleyl ether sodium sulfate, triethanolamine polyoxyethylene lauryl ether sulfate and the like and salts thereof; alkylaryl ether sulfuric acid and a salt thereof; alkylamide sulfuric acid and a salt thereof; and the like. These may be used alone, or two or more kinds thereof may be used in combination.

Of the above-mentioned sulfate type surfactants, alkyl sulfuric acid and a salt thereof, and polyoxyethylene alkyl ether sulfuric acid and a salt thereof are preferable, polyoxyethylene alkyl ether sulfuric acid and a salt thereof are more preferable, and polyoxyethylene alkyl ether sulfate is most preferable.

The content of component B in the liquid cleansing composition of the present invention, is preferably 1 wt % or more and, from the aspect of the amount of lather, more preferably 3 wt % or more, further preferably 5 wt % or more, still more preferably 10 wt % or more, of the liquid cleansing composition. In addition, the content of component B is preferably 50 wt % or less and, from the aspect of stability of dissolution state, more preferably 45 wt % or less, further preferably 40 wt % or less, still more preferably 30 wt % or less.

The weight ratio of component A and component B is preferably within the range of component A:component B=1:100000-1:10, more preferably 1:10000-1:100, further preferably 1:1000-1:500.

(Component C)

The liquid cleansing composition of the present invention preferably further contains (Component C) a polysaccharide-type polymer. When component A and component C are simultaneously present in the liquid cleansing composition, they interact and the both molecules are arranged with orientation. As a result, a synergistic effect is achieved to impart the cleansing composition with appropriate viscosity.

Examples of component C include natural plant polymer, natural microbial polymer, semisynthetic cellulose polymer, semisynthetic alginic acid polymer and the like. These may be chemically modified. Among these, natural microbial polymer and natural plant polymer are preferable, and natural microbial polymer is more preferable, since the viscosity can be increased with ease.

Examples of the natural microbial polymer include xanthan gum, succinoglycan, hyaluronic acid, curdlan, gellan gum and the like. Examples of the natural plant polymer include guar gum, quince seed, carageenan, glucomannan, agar, pectin, mannan, starch, galactan, gum arabic, gum tragacanth, locust bean gum and the like. These may be used alone, or two or more kinds thereof may be used in combination. Of these, xanthan gum, carageenan and guar gum are preferable in view of viscosity. Xanthan gum and guar gum are more preferable, and xanthan gum is most preferable, since they do not require heating for dispersing.

The content of component C in the liquid cleansing composition of the present invention is preferably 0.01 wt % or more, more preferably 0.05 wt % or more, further preferably 0.1 wt % or more, of the liquid cleansing composition. The content of component C is preferably 30 wt % or less and, from the aspect of stability of dissolution state, more preferably 20 wt % or less, further preferably 10 wt % or less, still more preferably 5 wt % or less.

The pH of the liquid cleansing composition of the present invention is not particularly limited as long as it does not inhibit the effect of the present invention. The pH of the liquid cleansing composition of the present invention is, from the aspects of appropriate amount of lather and stability of dissolution state, preferably 4.0 or more, more preferably 4.5 or more, further preferably 5.0 or more, still more preferably 5.5 or more, especially preferably 6.0 or more, particularly preferably 6.5 or more. The pH of the liquid cleansing composition of the present invention is, from the aspects of appropriate amount of lather and stability of dissolution state, preferably 11.0 or less, more preferably 10.5 or less, further preferably 10.0 or less, still more preferably 9.5 or less, especially preferably 9.0 or less, particularly preferably 8.5 or less.

While the liquid cleansing composition of the present invention is not particularly limited, it can be contained in a cosmetic agent. The form of the cosmetic agent in the present invention is not particularly limited, and can take any form such as liquid (including slurry), gel, paste and the like.

Specific examples of the cosmetic agent include cleansing foam, body shampoo, hair shampoo, eye washing agent, oral cleaning agent such as toothpaste and the like, shaving foam, makeup removing agent, cleansing agent and the like.

The cosmetic agent in the present invention can appropriately further contain, according to an object, a component generally used for cosmetic agents and the like, as long as the effect of the present invention is not inhibited. Specifically, a component such as oil, surfactant, thickener, preservative, flavor, UV absorber, moisturizer, physiological activity component, antioxidant, anti-inflammatory agent, antibacterial agent, adiaphoretic, chelating agent, neutralization agent, pH adjuster and the like can be added according to the specific use or form of the cosmetic agent.

The liquid cleansing composition of the present invention can be produced according to a conventional method to have any appropriate appearance without any particular limitation, such as transparent, white turbid or pearly appearance and the like.

EXAMPLES

The present invention is explained in more detail in the following by referring to Examples, which are not to be construed as limitative.

Each component shown in the left column of Table 1 was mixed and stirred according to a conventional method to give each liquid cleansing composition of Examples 1-9 and Comparative Examples 1-8, and subjected to the evaluation of the property thereof.

Sodium 2-tetradecanamido-2-butenate, sodium 2-decanamido-2-hexadecenate and sodium 2-dodecanamido-2-butenate used as component A were respectively synthesized as shown below.

Synthetic Example 1

2-dodecanamido-2-butenoic acid

Lauryl amide (26.03 g), 2-ketobutanoic acid (20.00 g) and toluene (280 g) were mixed, and the mixture was heated under reflux for 14 hr. After cooling, the precipitate was collected by filtration to give a crude product. The product was recrystallized from toluene and dried to give 2-dodecanamido-2-butenoic acid (20.43 g).

1H-NMR (400 MHz, CD3OD, r.t.): δ 6.83 (1 H, q, J=7.1 Hz), 2.35 (2 H, t, J=7.3 Hz), 1.76 (3 H, d, J=7.1 Hz), 1.68 (2 H, m), 1.47-1.24 (16 H, m), 0.92 (3 H, t, J=6.7 Hz)

ESI-MS (positive) m/z 284 [M+H]+ (negative) m/z 282 [M−H]−

Synthetic Example 2 sodium 2-dodecanamido-2-butenate

2-Dodecanamido-2-butenoic acid obtained in Synthetic Example 1 was dispersed in water, and 27 wt % aqueous sodium hydroxide solution was added dropwise. The mixture was neutralized and the concentration was adjusted with ion exchange water to give 10 wt % aqueous solution of sodium 2-dodecanamido-2-butenate.

Synthetic Example 3

2-tetradecanamido-2-butenoic acid

In the same manner as in Synthetic Example 1 except that myristyl amide (29.69 g) was used instead of lauryl amide, 2-tetradecanamido-2-butenoic acid was obtained.

Synthetic Example 4 sodium 2-tetradecanamido-2-butenate

In the same manner as in Synthetic Example 2 except that sodium 2-tetradecanamido-2-butenate obtained in Synthetic Example 3 was used instead of 2-dodecanamido-2-butenoic acid, sodium 2-tetradecanamido-2-butenate was obtained.

Synthetic Example 5

2-decanamido-2-hexadecenoic acid

In the same manner as in Synthetic Example 1 except that 2-ketohexanoic acid (25.49 g) was used instead of 2-ketobutanoic acid, 2-decanamido-2-hexenoic acid was obtained.

Synthetic Example 6 sodium 2-decanamido-2-hexenate

In the same manner as in Synthetic Example 2 except that 2-decanamido-2-hexenoic acid obtained in Synthetic Example 5 was used instead of 2-dodecanamido-2-butenoic acid, sodium 2-decanamido-2-hexenate was obtained.

(Evaluation Method)

(1) Moist Feeling after Washing

A step of washing with hands using 1.0 mL of each liquid cleansing composition and drying with a towel was consecutively repeated 5 times, and the moist feeling of the skin immediately thereafter was evaluated by 10 professional panelists according to the following criteria.

3: very moist
2: moist
1: somewhat dry
0: dry
⊙: average 2.5 points or more, ○: average not less than 1.5 points and less than 2.5 points, Δ: average not less than 0.5 point and less than 1.5 points, and ×: average less than 0.5 point.

(2) Amount of Lather

Each liquid cleansing composition (1.0 mL) was taken and lather was made on the palm for 5 min. The amount of lather was evaluated by 10 professional panelists according to the following criteria.

3: very much
2: somewhat much
1: somewhat less
0: less
⊙: average 2.5 points or more, ○: average not less than 1.5 points and less than 2.5 points, Δ: average not less than 0.5 point and less than 1.5 points, and ×: average less than 0.5 point.

(3) Viscosity

Each liquid cleansing composition (5.0 mL) was taken on the palm, and the condition thereof was evaluated by 10 professional panelists according to the following criteria.

3: the composition stays for 3 seconds or longer on the palm inclined 45 degrees
2: the composition stays for 1 second but falls in 3 seconds from the palm inclined 45 degrees
1: the composition can be maintained on the palm but almost immediately falls therefrom upon tilting
0: the composition is difficult to maintain on the palm and immediately falls therefrom upon tilting ⊙: average 2.5 points or more, ◯: average not less than 1.5 points and less than 2.5 points, Δ: average not less than 0.5 point and less than 1.5 points, and ×: average less than 0.5 point.

(4) pH measurement

Using a pH meter (Horiba, Ltd. (F-52)) calibrated with a predetermined buffered solution (pH 9.18, pH 6.86, pH 4.01), the pH of the liquid cleansing composition (50 ml) was measured.

of lather and viscosity. Of component A, sodium 2-dodecanamido-2-butenate and sodium 2-tetradecanamido-2-butenate were found to be superior to sodium 2-decanamido-2-hexenate.

Formulation Example 1

A cosmetic agent having the composition shown in Table 2 below was prepared.

TABLE 1

| component (wt %) | | Example | | | | | | | | |
|---|---|---|---|---|---|---|---|---|---|---|
| | | 1 | 2 | 3 | 4 | 5 | 6 | 7 | 8 | 9 |
| A | Sodium 2-tetradecanamido-2-butenate | | | | | 0.05 | | | | |
| | Sodium 2-decanamido-2-hexenate | | | | 0.05 | | | | | |
| | Sodium 2-dodecanamido-2-butenate | 0.05 | 0.05 | 0.05 | | | 0.05 | 0.05 | 0.05 | 0.05 |
| B | Coco glucoside | 15 | 15 | 15 | 15 | 15 | | | | |
| | decylglucoside | | | | | | 15 | 15 | | |
| | lauryl POE sulfate | | | | | | | | 15 | 15 |
| C | 3% xanthan gum | | 12 | | | | 12 | | | |
| | 3% carageenan | | | 12 | | | | 12 | | |
| | 3% locust bean gum | | | | 12 | | | | 12 | |
| | 3% guar gum | | | | | 12 | | | | 12 |
| citric acid (pH adjuster) | | q.s. | q.s. | q.s. | q.s. | q.s. | q.s. | q.s. | q.s. | q.s. |
| ion exchange water | | bal. | bal. | bal. | bal. | bal. | bal. | bal. | bal. | bal. |
| total | | 100 | 100 | 100 | 100 | 100 | 100 | 100 | 100 | 100 |
| pH | | 5.5 | 5.5 | 5.5 | 5.5 | 5.5 | 5.5 | 5.5 | 5.5 | 5.5 |
| moist feeling after washing | | ⊙ | ⊙ | ⊙ | ◯ | ◯ | ⊙ | ⊙ | ⊙ | ⊙ |
| amount of lather | | ⊙ | ⊙ | ⊙ | ◯ | ◯ | ⊙ | ⊙ | ⊙ | ⊙ |
| viscosity | | Δ | ⊙ | ⊙ | ⊙ | ⊙ | ◯ | ◯ | ⊙ | ⊙ |
| | | | Comparative Example | | | | | | | |
| component (wt %) | | 1 | 2 | 3 | 4 | 5 | 6 | 7 | 8 | |
| A | Sodium 2-tetradecanamido-2-butenate | | | | | | | | | |
| | Sodium 2-decanamido-2-hexenate | | | | | | | | | |
| | Sodium 2-dodecanamido-2-butenate | | | | | | | | | |
| B | Coco glucoside | 15 | 15 | 15 | 15 | | | | | |
| | decylglucoside | | | | | 15 | 15 | | | |
| | lauryl POE sulfate | | | | | | | 15 | 15 | |
| C | 3% xanthan gum | 12 | | | | 12 | | | | |
| | 3% carageenan | | 12 | | | | 12 | | | |
| | 3% locust bean gum | | | 12 | | | | 12 | | |
| | 3% guar gum | | | | 12 | | | | 12 | |
| citric acid (pH adjuster) | | q.s. | q.s. | q.s. | q.s. | q.s. | q.s. | q.s. | q.s. | |
| ion exchange water | | bal. | bal. | bal. | bal. | bal. | bal. | bal. | bal. | |
| total | | 100 | 100 | 100 | 100 | 100 | 100 | 100 | 100 | |
| pH | | 5.5 | 5.5 | 5.5 | 5.5 | 5.5 | 5.5 | 5.5 | 5.5 | |
| moist feeling after washing | | Δ | Δ | Δ | Δ | Δ | Δ | X | X | |
| amount of lather | | — | — | — | — | — | — | — | — | |
| viscosity | | — | — | — | — | — | — | — | — | | bal.: balance

The liquid cleansing composition of Example 1 showed good amount and quality of lather, and was superior in the moist feeling after washing.

The liquid cleansing compositions of Examples 2-9 showed good amount of lather and appropriate viscosity, and were superior in the moist feeling after washing.

Thus, even addition of a small amount of component A could afford a moist feeling without a decrease in the amount

TABLE 2

| shampoo | amount (wt %) |
|---|---|
| sodium 2-dodecanamido-2-butenate (Component A) | 0.80 |
| lauryl glucoside (50%)[*1] (Component B) | 9.00 |
| glyceryl caprate [*2] | 3.00 |
| cocamidopropyl betaine (31%)[*3] | 15.00 |
| xanthan gum (3%) (Component C) | 12.00 |

TABLE 2-continued

| shampoo | amount (wt %) |
| --- | --- |
| flavor | q.s. |
| magnesium chloride | 1.50 |
| citric acid | 0.08 |
| water | balance |
|  | 100.00 |

*[1]PLANTACARE 1200UP (Cognis Japan Ltd.)
*[2] SUNSOFT No. 760 (Taiyo Kagaku Co., Ltd.)
*[3]DEHYTON K (Cognis Japan Ltd.)
pH 6.5

Formulation Example 2

A cosmetic agent having the composition shown in Table 3 below was prepared.

TABLE 3

| face cleansing agent | amount (wt %) |
| --- | --- |
| guar gum (3%) (Component C) | 12.00 |
| sodium 2-dodecanamido-2-butenate (Component A) | 1.00 |
| Na laureth sulfate (25%)*[4] (Component B) | 20.00 |
| polyquaternium-39*[5] | 0.20 |
| sodium hydroxide | 0.26 |
| water | balance |
| flavor | q.s. |
|  | 100.00 |

*[4]EMAL 20C (Kao Corporation)
*[5]MERQUAT PLUS 3330 (Matsumoto Trading Co., Ltd.)
pH 6.1

The cosmetic agents of Formulation Examples 1 and 2 showed good amount of lather, and were superior in the moist feeling after washing.

INDUSTRIAL APPLICABILITY

By combining a particular alkenoic acid or a salt thereof with a sugar type surfactant and/or a sulfate type surfactant, a liquid cleansing composition showing a good amount of lather and superior moist feeling after washing can be provided.

This application is based on a patent application No. 2011-102517 filed in Japan, the contents of which are incorporated in full herein.

The invention claimed is:

1. A liquid cleansing composition, comprising
(A) at least one compound represented by formula (1):

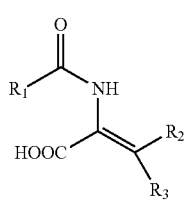

(1)

wherein $R_1$ is a saturated or unsaturated, linear or branched-chain hydrocarbon group having a carbon number of 11 to 25, and $R_2$ and $R_3$ are each independently a hydrogen atom or an alkyl group having a carbon number of 1 to 6, or a salt thereof; and
(B) at least one sugar type surfactant and/or at least one sulfate type surfactant.

2. A liquid cleansing composition according to claim 1, wherein $R_2$ and $R_3$ are each independently a hydrogen atom or an alkyl group having a carbon number of 1 to 5.

3. A liquid cleansing composition according to claim 1, wherein $R_1$ is a saturated or unsaturated, linear or branched-chain hydrocarbon group having a carbon number of 11 to 13.

4. A liquid cleansing composition according to claim 1, wherein one of $R_2$ and $R_3$ is a methyl group, and the other is a hydrogen atom.

5. A liquid cleansing composition according to claim 1, wherein said at least one compound represented by formula (1) is 2-dodecanamido-2-butenoic acid or a salt thereof.

6. A liquid cleansing composition according to claim 1, wherein said at least one compound represented by formula (1) is present in an amount of not less than 0.0001 wt % and not more than 1 wt %, based on the total weight of said liquid cleansing composition.

7. A liquid cleansing composition according to claim 1, wherein said at least one sugar type surfactant is an alkylglucoside.

8. A liquid cleansing composition according to claim 1, wherein said at least one sulfate type surfactant is a polyoxyethylene alkyl ether sulfuric acid or a salt thereof.

9. A liquid cleansing composition according to claim 1, further comprising:
(C) at least one polysaccharide-type polymer.

10. A liquid cleansing composition according to claim 9, wherein said at least one polysaccharide-type polymer is one or more kinds selected from the group consisting of xanthan gum, carageenan, locust bean gum, guar gum, pectin, and succinoglycan.

11. A cosmetic agent, comprising a liquid cleansing composition according to claim 1.

12. A method of improving the moist feeling after washing afforded by a liquid cleansing composition, said method comprising adding:
(A) at least one compound represented by formula (1)

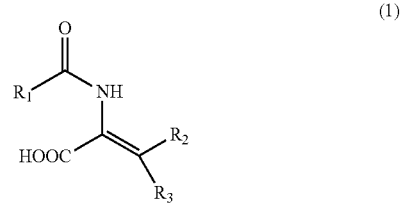

(1)

wherein $R_1$ is a saturated or unsaturated, linear or branched-chain hydrocarbon group having a carbon number of 11 to 25, and $R_2$ and $R_3$ are each independently a hydrogen atom or an alkyl group having a carbon number of 1 to 6, or a salt thereof, to a cleansing composition which comprises:
(B) at least one sugar type surfactant and/or at least one sulfate type surfactant.

13. A method according to claim 12, wherein $R_2$ and $R_3$ are each independently a hydrogen atom or an alkyl group having a carbon number of 1 to 5.

14. A method according to claim 12, wherein $R_1$ is a saturated or unsaturated, linear or branched-chain hydrocarbon group having a carbon number of 11 to 13.

15. A method according to claim 12, wherein one of $R_2$ and $R_3$ is a methyl group and the other is a hydrogen atom.

16. A method according to claim 12, wherein said at least one compound represented by formula (1) is 2-dodecanamido-2-butenoic acid or a salt thereof.

17. A method according to claim 12, wherein said at least one compound represented by formula (1) is added in an amount such that the content of said at least one compound represented by formula (1) in said liquid cleansing composition is not less than 0.0001 wt % and not more than 1 wt %, based on the total weight of said liquid cleansing composition.

18. A method according to claim 12, wherein said at least one sugar type surfactant is an alkylglucoside.

19. A method according to claim 12, wherein said at least one sulfate type surfactant is a polyoxyethylene alkyl ether sulfuric acid or a salt thereof.

20. A method according to claim 12, wherein said cleansing composition further comprises:
    (C) at least one polysaccharide-type polymer.

21. A method according to claim 20, wherein said at least one polysaccharide-type polymer is one or more kinds selected from the group consisting of xanthan gum, carageenan, locust bean gum, guar gum, pectin, and succinoglycan.

\* \* \* \* \*